United States Patent [19]

Maeda et al.

[11] Patent Number: 5,492,903
[45] Date of Patent: Feb. 20, 1996

[54] CRYSTALLINE ESTERS OF (+)-(5R, 6S)-6-[(R)-1-HYDROXYETHYL]-3-(3-PYRIDYL)-7-OXO-4-THIA-1-AZABICYCLO[3.2.0]HEPT-2-ENE-2-CARBOXYLIC ACID

[75] Inventors: Yoshiharu Maeda, Tondabayashi; Yukio Ishibashi, Toyonaka; Tetsuya Tsukamoto, Nishinomiya; Masahiro Mizuno, Takatsuki, all of Japan

[73] Assignee: Takeda Chemical Industries Ltd., Osaka, Japan

[21] Appl. No.: 112,072

[22] Filed: Aug. 26, 1993

Related U.S. Application Data

[63] Continuation-in-part of Ser. No. 834,862, Feb. 13, 1992, abandoned, and a continuation-in-part of Ser. No. 76,947, Jun. 16, 1993, abandoned, which is a continuation of Ser. No. 713,519, Jun. 12, 1991, abandoned.

[30] Foreign Application Priority Data

| Jun. 19, 1990 | [JP] | Japan | 2-160597 |
| Oct. 1, 1990 | [JP] | Japan | 2-264580 |
| Feb. 15, 1991 | [JP] | Japan | 3-044307 |
| May 8, 1991 | [JP] | Japan | 3-102629 |

[51] Int. Cl.$^6$ .................... C07D 499/00; A61K 31/425
[52] U.S. Cl. ................ 514/195; 514/192; 540/310; 540/312
[58] Field of Search ................ 540/310; 514/192, 514/195

[56] References Cited

U.S. PATENT DOCUMENTS

| 4,006,138 | 2/1977 | Yang | 260/243 C |
| 4,634,556 | 1/1987 | Jenkins et al. | 540/310 |
| 4,748,238 | 5/1988 | Shih | 540/350 |
| 4,826,832 | 5/1989 | Lang | 514/192 |

FOREIGN PATENT DOCUMENTS

| 246187 | 11/1987 | European Pat. Off. . |
| 60-52751 | 11/1985 | Japan . |
| WO9001484 | 2/1990 | WIPO . |

OTHER PUBLICATIONS

Bedeschi et al., *The Journal of Antibiotics*, "Synthesis and Structure–Activity Relations in the Class of 2–(Pyridyl)Penems", vol. XLIII, No. 3, Mar. 1990, pp. 306–313.

*Chemical Abstracts*, vol. 97, No. 5, Aug. 1982, No. 97:38753p.

Pikal et al., *Journal of Pharmaceutical Sciences*, "Thermal Decomposition of Amorphous β–Lactam Antibacterials," vol. 66, No. 9, Sep. 1977, pp. 1312–1316.

*Primary Examiner*—Nicholas Rizzo
*Attorney, Agent, or Firm*—Foley & Lardner

[57] ABSTRACT

Crystalline acetoxymethyl and pivaloyloxymethyl esters of (+)-(5R, 6S)-6-[(R)-1-hydroxyethyl]-3-(3-pyridyl)-7-oxo-4-thia-1-azabicyclo-[3.2.0]hept-2-ene-carboxylic acid can be obtained by adding a poor solvent to a solution of acetoxymethyl or pivaloyloxymethyl ester of (+)-(5R, 6S)-6-[(R)-1-hydroxyethyl]-3-(3-pyridyl)-7-oxo-4-thia-1-azabicyclo-[3.2.0]hept-2-ene-carboxylic acid in a good solvent. The crystalline penem compounds obtained show improved stability and are useful antibacterial agents.

7 Claims, 3 Drawing Sheets

CRYSTALLINE ESTERS OF (+)-(5R, 6S)-6-[(R)-1-HYDROXYETHYL]-3-(3-PYRIDYL)-7-OXO-4-THIA-1-AZABICYCLO[3.2.0] HEPT-2-ENE-2-CARBOXYLIC ACID

CROSS-REFERENCE TO RELATED APPLICATIONS

This application is a continuation-in-part of Ser. No. 834,862 filed Feb. 13, 1992, now abandoned, and Ser. No. 076,947 filed Jun. 16, 1993, now abandoned, which in turn is a continuation of Ser. No. 713,519 filed Jun. 12, 1991, now abandoned.

BACKGROUND OF THE INVENTION

Amorphous esters of (+)-(SR, 6S)-6-[(R)-1-hydroxyethyl]-3-(3-pyridyl)-7-oxo-4-thia-1-azabicyclo[3.2.0]hept-2-ene-2-carboxylic acid are known compounds. There is no disclosure in the prior art of any crystalline form, and particularly not an acetoxymethyl or pivaloyloxymethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid.

It is recognized in the general art of crystallization of chemical compounds which include the instant acetoxymethyl and pivaloyloxymethyl esters of (+)-(5R, 6S)-6-[(R)-1-hydroxyethyl]-3-(3-pyridyl)-7-oxo-4-thia-1-azabicyclo [3.2.0 ]hept-2-ene-2 carboxylic acid that "it is very difficult, though not absolutely impossible, to predict which crystal form is taken by a chemical substance which has never crystallized" as well as "the first crystal is often difficult to obtain of a newly discovered or synthesized chemical substance . . . once crystallization is successfuly achieved somewhere in the world, the substance becomes easily crystallizable; crystallization becomes easier and easier as the crystallization frequency increases" as stated by Prof. Rupert Sheldrake in *The New Scientists* (1989), "cephalosporins are often difficult to obtain in crystalline form and, even when crystallized, the products may be partially amorphous" as stated in *Jour. Pharm. Sciences,* 66, p. 1312 [near bottom left column] (1977) and "attempts to prepare cefamandole sodium in crystalline form suitable for commercial use with respect to purity and long-term stability were unsuccessful" as stated in *Jour. Pharm. Sciences,* 65, p. 1175 (1976).

There is a recognition in the art that any crystallization of penem compounds is often attainable, if at all, only with inventive skill, i.e., one of ordinary skill in the art is often not able to synthesize a crystalline form of a given penem compound. There is no relevant teaching in the prior art known to applicants that relates to a compound structurally close to either the acetoxymethyl or pivaloyloxymethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid that leads to the synthesis set forth in this specification for the preparation of the crystalline acetoxymethyl or pivaloyloxymethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid. Applicants have considered the patents to both Jenkins, U.S. Pat. No. 4,634,556 ("Jenkins") and Lang, U.S. Pat. No. 4,826,832 ("Lang") which teach away from the successful synthesis of the crystalline acetoxymethyl or pivaloyloxymethyl ester of (+)-(5R, 6S)-6-[(R)-1-hydroxyethyl]-3-(3-pyridyl)-7-oxo-4-thia-1-azabicyclo [3.2.0 ] hept-2-ene-2 carboxylic acid. Considering the Jenkins patent, it is remote from the instant esters in terms of being an entirely different structure which does not provide motivation leading to the instant invention. First, Jenkins has a carbamoyloxyethylthio group which is neither an aromatic group nor a cyclic group but only a chain group attached with a sulfur atom to the 2-position of the penera nucleus, while Lang has either a 3-(or 4)-pyridyl group which is an aromatic heterocyclic group attached to the carbon atom at the same $R^3$ position. Second, the gross structural differences between Lang and Jenkins do not permit their combination for any teaching insofar as any predictability is concerned for the creation of a crystalline form as per the present invention, inter alia, the carbamoyloxyethylthio group is entirely different from a pyridyl group as one is not aromatic whereas the other is, one is non-cyclic while the other is heterocyclic and one is bonded through carbon while the other is bonded through sulfur. Third, Jenkins teaches a structure that is grossly different from the instant acetoxymethyl or pivaloyloxymethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid ester in that Jenkins' compound is a simple sodium salt —COONa whereas the instant compounds are each an oxymethyl ester

—COOCH$_2$O—.

Fourth, the instant esters are from a (+)-(5R, 6S)-6-[(R)-1-hydroxyethyl]-3-(3-pyridyl)-7-oxo-4-thia-1-azabicyclo [3.2.0]hept- 2-ene-2-carboxylic acid whereas Jenkins' compound has at the 3-position the group

—S—CH$_2$—CH$_2$—C(=O)—NH$_2$ which is grossly dissimilar from the pyridyl required in the compound acetoxymethyl ester of (+)-(5R, 6S)-6-[(R)-1-hydroxyethyl]-3-(3-pyridyl)-7-oxo-4-thia-1-azabicyclo [3.2.0]hept-2-ene-2-carboxylic acid. Fifth, it is further manifested to a worker skilled in the art that salts and esters in the penem field will have differing solubilities to further remove any predictive value from Jenkins vis a vis crystallization of the instant compound and manifestly is not combinable with any teachings of Lang insofar as the instant invention is concerned. The prior art, taken alone or together with the skill of a worker in the art, does not provide a basis for the synthesis of any crystalline acetoxymethyl or pivaloyloxymethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid.

One of ordinary skill in the art, given his ordinary skill and the teachings of the prior art, would not have been able to synthesize any crystalline acetoxymethyl or pivaloyloxymethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid in any form. Crystalline acetoxymethyl or pivaloyloxymethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid provides advantages over the amorphous form of the same compound because only the crystalline form is capable of prolonged storage without disintegration as manifested by color changes and the amorphous form is not attainable in the same level of purity as the crystalline form. The superior properties of the crystalline form make such form suitable as a medication whereas an amorphous form of this compound is unsuitable for general medicinal use.

The tests set forth below confirm that whereas the amorphous compound of Reference Example 4 was unstable after three days when measured at extreme temperatures of 40° C., 50° C. and 60° C. showing residual rate values of 95.6%, 83.7% and 55.8%, respectively, the crystalline acetoxymethyl ester of (+)-(5R, 6S)-6-[(R)-1-hydroxyethyl-]-3-(3-pyridyl)-7-oxo-4-thia-1-azabicyclo[3.2.0]hept-2-ene-2-carboxylic acid demonstrated storage stability under the identical conditions of in excess of 100.0%, i.e., measured at 40° C., 50° C. and 60° C., storage stability was 101.9%, 101.7% and 102.2%, respectively. The test of the foregoing paragraph are standard industry tests to determine storage stability, and the results of the test indicate that the amorphous powder is not storage stable and therefor not satisfactory to be marketed as a pharmaceutical while the instant crystalline acetoxymethyl ester of (+)-(5R, 6S)-6-[(R)-1-hydroxyethyl]-3-(3-pyridyl)-7-oxo-4-thia-1-azabicyclo [3.2.0]hept-2-ene-2-carboxylic acid is storage stable.

It is also noted that the sodium salt of (+)-(5R, 6S)-6-[(R)-1-hydroxyethyl]-3-(3-pyridyl)-7-oxo-4-thia-1-azabicyclo[3.2.0]hept-2-ene-2-carboxylic acid is known. However, the sodium salt is not used in the method of the invention to make a crystalline ester of (+)-(5R, 6S)-6-[(R)-1-hydroxyethyl]-3-(3-pyridyl)-7-oxo-4-thia-1-azabicyclo [3.2.0]hept-2-ene-2-carboxylic acid. It has been discovered that the potassium salt provides unexpectedly easier crystallization and improved yield and reactivity in comparison to the sodium salt.

SUMMARY OF THE INVENTION

The invention in a first aspect relates to crystalline esters of (+)-(5R, 6S )-6-[(R)-1-hydroxyethyl]-3-(3-pyridyl )-7-oxo-4-thia-1-azabicyclo [3.2.0]hept-2-ene-2-carboxylic acid which are the pivaloyloxymethyl and acetoxymethyl esters.

In a second aspect of the invention there is provided a method for making said crystalline esters of (+)-(5R, 6S)-6-[(R)-1-hydroxyethyl]-3-(3-pyridyl)-7-oxo-4-thia-1-azabicyclo [3.2.0]hept-2-ene-2-carboxylic acid.

In a third aspect of the invention there is provided potassium (+)-(5R, 6S)-6-[(R)-1-hydroxyethyl]-3-(3-pyridyl)-7-oxo-4-thia-1-azabicyclo [3.2.0]hept-2-ene-2-carboxylate which is a starting material for the aforementioned method for making said crystalline esters of (+)-(5R, 6S)-6-[(R)-1-hydroxyethyl]-3-(3-pyridyl)-7-oxo-4-thia-1-azabicyclo [3.2.0]hept-2-ene-2-carboxylic acid.

DETAILED DESCRIPTION OF THE INVENTION

The Pivaloyloxymethyl Ester

Figure 1:
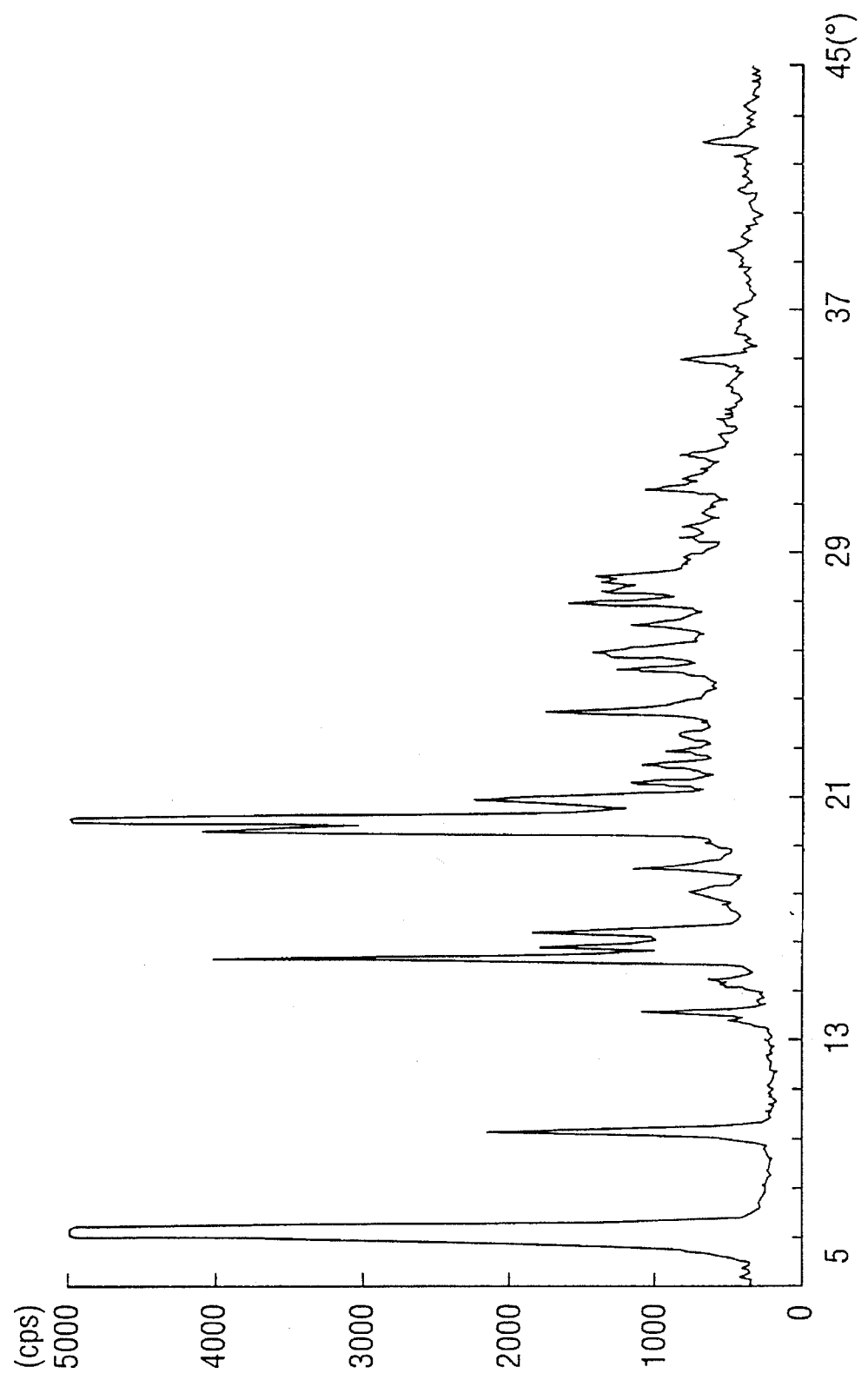
FIG. 1 is a powder X-ray diffraction pattern of the crystalline (+)-(5R, 6S)-6-[(R)-1-hydroxyethyl]-3-(3-pyridyl)-7-oxo-4-thia-1-azabicyclo [3.2.0]hept-2-ene-2-carboxylic acid pivaloyloxymethyl ester of the present invention.

According to the present invention, there is provided crystalline (+)-(5R, 6S)-6-[(R)-1-hydroxyethyl]-3-(3-pyridyl)-7-oxo-4-thia-1-azabicyclo[3.2.0]hept-2-ene-2-carboxylic acid pivaloyloxymethyl ester having a diffraction pattern which shows main peaks at spacing of 12.8, 8.8, 5.6, 4.44, 4.36, and 4.2 Å according to powder X-ray diffraction.

The crystalline penem compound is obtained by dissolving amorphous (+)-(5R, 6S)-6-[(R)-1-hydroxyethyl]-3-(3-pyridyl)-7-oxo-4-thia-1-azabicyclo[3.2.0]hept-2-ene-2-carboxylic acid pivaloyloxymethyl ester in a good solvent, adding thereto a poor solvent which is miscible with the good solvent, stirring the mixture and then cooling to a temperature of not higher than 30° C. The present invention also provides this production process as well as an antibacterial agent comprising the crystalline penem compound.

The amorphous (+)-(5R, 6S)-6-[(R)-1-hydroxyethyl]-3-(3-pyridyl)-7-oxo-4-thia-1-azabicyclo[3.2.0]hept-2-ene-2-carboxylic acid pivaloyloxymethyl ester to be used in the present invention can be obtained by esterifying its sodium salt with methylpivalate iodide according to the disclosure of U.S. Pat. No. 4,826,832.

Examples of the good solvent of the amorphous penem compound include lower alcohols such as methanol, ethanol, propanol, isopropanol and the like and esters such as ethyl acetate and the like. Upon crystallization, if necessary, it is heated up to about 40° C. to dissolve the amorphous penem compound in the good solvent. The concentration of the amorphous penem compound is not specifically limited but, in view of higher yield of the crystal, the concentration is preferably made as high as possible. In the present invention, a reaction mixture from the esterification step in the production of the penem compound may be used directly without isolation of the amorphous penem compound by diluting the reaction mixture with the good solvent, purified and then optionally concentrated, preferably, under reduced pressure.

Examples of the poor solvent which is miscible with the good solvent include water in the case of using an alcohol as the good solvent as well as ethyl ether, n-hexane, petroleum ether and the like in the case of using an ester as the good solvent. The poor solvent is added in an amount sufficient for crystallization of the penem compound. Normally, the volume ratio of the good solvent to the bad solvent is about 1:1.5 to 10.

When the mixture of the poor solvent and good solvent containing the penem compound is stirred at a temperature of, normally, room temperature to 35° C. (−10° to 35° C.) for 5 minutes to 2 hours, the crystallization of the penem compound is started. In this case, the crystallization can be promoted, for example, by rubbing the wall of a container or the like according to a conventional method. Then it is cooled to 30° C. or lower, preferably −5° to 15° C. and, further, stirred for 30 minutes to 20 hours, or allowed to stand to complete crystallization. The resulting crystals are washed, dried and then isolated according to a conventional method.

The crystalline penem compound thus obtained according to the present invention has a melting point of about 95° to 96° C. and shows a diffraction pattern having main peaks at spacing of 12.8, 8.8, 5.6, 4.44, 4.36 and 4.2 A according to powder X-ray diffraction.

The crystalline penem compound is useful as an antibiotic having broad antibacterial spectrum by oral administration. For example, the penem compound have a minimum inhibitory concentration of about 8 μg/ml or less against both gram-positive and gram-negative bacteria such as *Staphylococcus aureus, Staphylococcus pyogenes, Streptococcus pneumoniae, Streptococcus faealis* and bacteria of the genus Neisseria. In addition, it has a minimum inhibitory concentration of about 64 μl/ml or less against gram-negative rod bacteria such as those of the genus Enterobacter, *Haemophilus influenzae*, bacterial of the genus Pseudomonas and the like and aerobic bacteria such as the genus Baceroides. Further, in mouse systematic infection caused by *Streptococcus aureus*, it has $ED_{50}$ of about 0.5 to 15 mg/kg by oral administration.

Therefore, the crystalline penem compound of the present invention can be used as an agent for treatment and prevention of bacterial infectious diseases of human and other mammal, for example, respiratory infectious diseases, urinary tract infectious diseases, suppurative diseases, biliary infectious diseases, enteral infectious diseases, obstetrics and gynecology infectious diseases, otorhinology infectious diseases, surgery infectious diseases and the like.

For oral administration, the crystals are formulated in the form of tablets or capsules according to a conventional method, which can contain various additives, for example, diluents such as lactose, glucose, sucrose, mannitol, sorbitol, cellulose, glycine, etc.; lubricants such as silica, talc, stearic acid or its salt, polyethylene glycol, etc.; binders such as aluminum magnesium silicate, starch, gelatin, gums, cellulose derivatives, polypyrrolidone, etc.; disintegrators such as starch, alginic acid or its salt, etc.; colorants; flavors; sweeteners and the like.

The dosage varies depending upon a particular patient, conditions of diseases and the like. Usually, for an adult patient of 70 kg in body weight, the desired effect can be obtained by oral administration of about 50 mg to 1 g per day.

As described above, according to the present invention, crystalline (+)-(5R, 6S)-6-[(R)-1-hydroxyethyl]-3-(3-pyridyl)-7-oxo-4-thia-1-azabicyclo[3.2.0]hept-2-ene-2-carboxylic acid pivaloyloxymethyl ester having excellent antibacterial activity and storage stability can be obtained, particularly, from a water-ethanol system which is beneficial from the viewpoint of the residual solvent. Therefore, the crystalline penem compound is an extremely useful medicine.

The present invention further provides a novel penem compound of the formula (I):

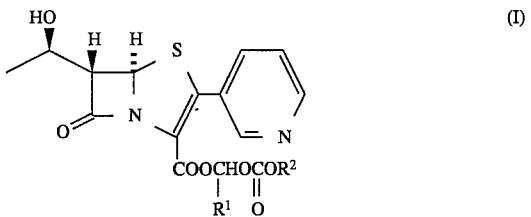

wherein $R^1$ is hydrogen atom or a lower alkyl; and $R^2$ is an alkyl group branched at α position or a cycloalkyl. The penem compound (I) also manifests excellent antibacterial activities against not only gram negative bacteria but also gram-positive bacteria by oral administration and has good properties for medicines such as good absorbability, low toxicity, good stability and the like. In the compound (I), examples of the lower alkyl group represented by $R^1$ include $C_{1-6}$ alkyl such as methyl, ethyl, propyl, isopropyl and the like. A preferred example of the alkyl of $R^1$ is methyl or ethyl.

Examples of the alkyl group branched at α position represented by $R^2$ include $C_{3-10}$ alkyl branched at α position such as isopropyl, sec-butyl, 1-ethylpropyl, 1-methylbutyl, 1-ethylbutyl, 1-methylpentyl, 1-propylbutyl, 1-butylpentyl and the like. A preferred example of the alkyl group branched at α position of $R^2$ is isopropyl. Examples of the cycloalkyl group represented by $R^2$ include $C_{3-10}$ cycloalkyl such as cyclopropyl, cyclobutyl, cyclopentyl, cyclohexyl, cycloheptyl, 2-methylcyclohexyl, 3-methylcyclohexyl, 2-isopropyl-5-methylcyclohexyl and the like. A preferred example of the cycloalkyl of $R^2$ is cyclohexyl.

The compound (I) can be produced by reacting (+)-(5R, 6S)-6-[(R)-1-hydroxyethyl]-3-(3-pyridyl)-7-oxo-4-thia-1-azabicyclo[3.2.0]hept-2-ene-2-carboxylic acid or its salt (e.g. a salt with an alkali metal such as sodium, potassium, etc.) with a compound of the formula (II):

wherein $R^1$ and $R^2$ are as defined above and X is a halogen atom such as iodine, bromine, chlorine, fluorine or the like.

Usually, this reaction is conducted in an organic solvent. An organic solvent can be used insofar as it does not adversely affect the reaction. Examples of the organic solvent include hydrocarbons such as hexane, benzene, toluene, xylene and the like, ethers such as tetrahydrofuran, isopropyl ether, dioxane, diethyl ether and the like, halogenated hydrocarbons such as methylene chloride, carbon tetrachloride and the like, esters such as ethyl acetate and the like, ketones such as acetone and the like, amides such as N,N-dimethylformamide, N,N-dimethylacetamide and the like, and a mixture thereof. Preferred examples of the solvent are amide such as N,N-dimethylformamide, N,N-dimethylacetamide and the like. The reaction temperature is not specifically limited insofar as the esterification reaction proceeds. Usually, the reaction is conducted at −50° to 80° C., preferably −30° to 30° C. The reaction time varies depending upon the particular compound (II), solvent, reaction temperature and the like but, preferably, the reaction is conducted within about several hours, more preferably, for 1 to 30 minutes. The amount of the compound (II) to be used is normally about 1 to 2 moles, preferably, 1 to 1.5 moles based on 1 mole of (+)-(5R, 6S)-6-[(R)-1-hydroxyethyl]-3-(3-pyridyl)-7-oxo-4-thia-1-azabicyclo[3.2.0]hept-2-ene-2-carboxylic acid or its salt.

It has been found that the potassium salt of (+)-(5R, 6S)-6-[(R)-1-hydroxyethyl]-3-(3-pyridyl)-7-oxo-4-thia-1-azabicyclo[3.2.0]hept-2-ene-2-carboxylic acid is very useful for the production of the compound (I) in comparison with the corresponding known sodium salt because the sodium salt powder is hardly crystallized, while the potassium salt is readily crystallized and, upon producing the compound (I), it is superior in reactivity as well as the yield and purity of the desired ester compound (I) and the like to the sodium salt.

The compound (I) thus obtained can be isolated and purified by known means such as solvent extraction, conversion of liquid properties, concentration, crystallization, recrystallization, chromatography and the like.

The starting compound used in the production of the compound (I), (+)-(5R, 6S)-6-[(R)-1-hydroxyethyl]-3-(3-pyridyl)-7-oxo-4-thia-1-azabicyclo[3.2.0]hept-2-ene-2-carboxylic acid or its salt, can be produced by, for example, the process disclosed in U.S. Pat. No. 4,826,832 or a modification thereof. The compound (II) an be produced by, for example, the process disclosed in J. Antibiotics, 40, 81–90 (1987); and J. Antibiotics, 40, 370–384 (1987), or a modification thereof.

The preferred examples of the compound (I) are as follows:

(+)-(5R, 6S)-6-[(R)-1-hydroxyethyl]-3-(3-pyridyl)-7-oxo-4-thia-1-azabicyclo[3.2.0]hept-2-ene-2-carboxylic acid 1-(cyclohexyloxycarbonyloxy)ethyl ester, (+)-(5R, 6S)-6-[(R)-1-hydroxyethyl]-3-(3-pyridyl)-7-oxo-4-thia-1-azabicyclo[3.2.0]hept-2-ene-2-carboxylic acid cyclohexyloxycarbonyloxymethyl ester, (+)-(5R, 6S)-6-[(R)-1-hydroxyethyl]-3-(3-pyridyl)-7-oxo-4-thia-1-azabicyclo[3.2.0]hept-2-ene-2-carboxylic acid 1-(isopropoxycarboyloxy)ethyl ester, (+)-(5R, 6S)-6-[(R)-1-hydroxyethyl]-3-(3-pyridyl)-7-oxo-4-thia-1-azabicyclo[3.2.0]hept-2-ene-2-carboxylic acid isopropoxycarbonyloxymethyl ester.

The compound (I) has the same antibacterial spectrum as that described with respect to the above pivaloyloxymethyl ester and can be administered orally according to the same manner as described above. Further, they can be formulated in a pharmaceutical composition according to the same manner as that described with respect to the above pivaloyloxymethyl ester.

The following Reference Examples, Examples and Experiment further illustrate the present invention in detail but are not to be construed to limit the scope thereof.

The symbols used in the Reference Examples and Examples mean as follows:

s: singlet, br: broad, d: doublet, q: quartet, m: multiplet, ABq: AB type quartet, $CDCl_3$: deuterio chloroform, DMSO-$d_6$: dimethylsulfoxide-$d_6$, $D_2O$: heavy water and %: % by weight.

Reference Example 1

The silver salt (6.96 g) of 2-[(3S, 4R)-3-[(R)-1-allyloxycarbonyloxyethyl]-4-mercapto-2-oxoazetidin-1-yl]-2-triphenylphosphoranilidene acetic acid allyl ester was dissolved in methylene chloride (110 ml), to which were added pyridine (3.2 ml), 4-dimethylaminopyridine (200 mg) and then nicotinoyl chloride hydrochloride (2.68 g) at 0° C., and the mixture was stirred for 20 minutes. The solid formed was filtered off and the filtrate was washed in turn with sodium bicarbonate and saturated sodium chloride solution. After drying over anhydrous magnesium sulfate, the solvent was distilled off an the residue was subjected to a silica gel chromatography by eluting with toluene-ethyl acetate (9:1 to 3:2) to obtain 2-[(3S, 4R)-3-[(R)-1-allyloxycarbonyloxyethyl]-4-nicotinoylthio-2-oxoazetidin-yl]-2-triphenylphosphoranilidene acetic acid allyl ester [TLC: $R_f$=0.33 (silica gel, ethyl acetate)].

The ester of the penem compound thus obtained (3.1 g) was dissolved in toluene 600 ml) and the mixture was stirred at the reflux temperature for 3 hours under argon atmosphere. The solvent was evaporated and the residue was subjected to a silica gel chromatography by eluting with toluene-ethyl acetate (9:1 to 85:15) to obtain (5R, 6S)-6[(R)-1-allyloxycarbonyloxyethyl]-3-(3-pyridyl)-7-oxo-4-thia-1-azabicyclo[3.2.0]hept-2-ene-carboxylic acid allyl ester (TLC: $R_f$=0.5 (silica gel, ethyl acetate)].

The allyl ester (1.1 g) of the penem compound thus obtained was dissolved in tetrahydrofuran (48 ml) and to this were added tetrakis(triphenylphosphine)palladium (111 mg) and tributyl tin hydride (1.6 ml). After stirring at room temperature for 35 minutes, acetic acid (0.36 ml) was added dropwise. The mixture was further stirred for 30 minutes and concentrated by a rotary evaporator. The residue was added to water-ethyl acetate and then neutralized with sodium bicarbonate. The aqueous layer was washed twice with ethyl acetate and concentrated under vacuum. Then, it was subjected to a chromatography on $OptiUPC_{12}$ by eluting with water to obtain the corresponding sodium salt [TLC: $R_f$=0.61 ($OptiUPC_{12}$, water)].

The sodium salt thus obtained (62 g) was dissolved in dimethyl formamide (1.5 ml). After cooling to 0° C., methylpivalate iodide (53 ul) was added. After stirring for one hour, the reaction mixture was diluted with ethyl acetate, washed three times with a saturated sodium chloride solution, dried and then concentrated. The residue was subjected to a silica gel chromatography by eluting with toluene-ethyl acetate (3:1 to 1:1) to obtain the corresponding pivaloyloxymethyl ester (TLC: $R_f$=0.34 (silica gel, ethyl acetate)].

This product was a hydroscopic powder and it was confirmed to be amorphous by X-ray diffraction.

Reference Example 2

Potassium hydroxide (67.3 g) was suspended in tetrahydrofuran (1.2 liters) and to the suspension was added 2-ethylhexanoic acid (173.1 g) was added. The mixture was stirred until potassium hydroxide was dissolved to obtain a solution of potassium 2-ethylhexanoate.

(+)-(5R, 6S)-6-[(R)-1-hydroxyethyl]-3-(3-pyridyl)-7-oxo-4-thia-1-azabicyclo[3.2.0]hept-2-ene-2-carboxylic acid allyl ester (332.4 g) was dissolved in a mixture of methylene chloride (2.5 liters) and tetrahydrofuran (1.3 liters). To the solution were added triphenylphosphine (26.2 g) and tetrakis(tripheylphosphine)palladium (11.6 g), followed by further addition of the above solution of potassium 2-ethylhexanoate. The mixture was stirred for 15 minutes and ethyl ether was added dropwise thereto to deposit crystals. After stirring for 30 minutes, the crystals were corrected by filtration and washed with ethyl ether (2 liters). The crystals were dried under reduced pressure to obtain crude crystals of potassium (+)-(5R, 6S)-6-[(R)-1-hydroxyethyl]-3-(3-pyridyl)-7-oxo-4-thia-1-azabicyclo[3.2.0]hept-2-ene-2-carboxylate.

The crude crystals were dissolved in a mixture methanol (460 ml) and water (230 ml) and to the solution was added dropwise acetonitrile (7.0 liters) to deposit crystals. The mixture was cooled to 10° C. or lower and allowed to stand for 1 hour. The crystals were corrected by filtration and washed with acetonitrile (3.5 liters) and dried under reduced pressure to obtain crystals of potassium (+)-(5R, 6S)-6-[(R)-1-hydroxyethyl ] -3-(3-pyridyl)-7-oxo-4-thia-1-azabicyclo [3.2.0]hept-2-ene-2-carboxylate.

Figure 2:
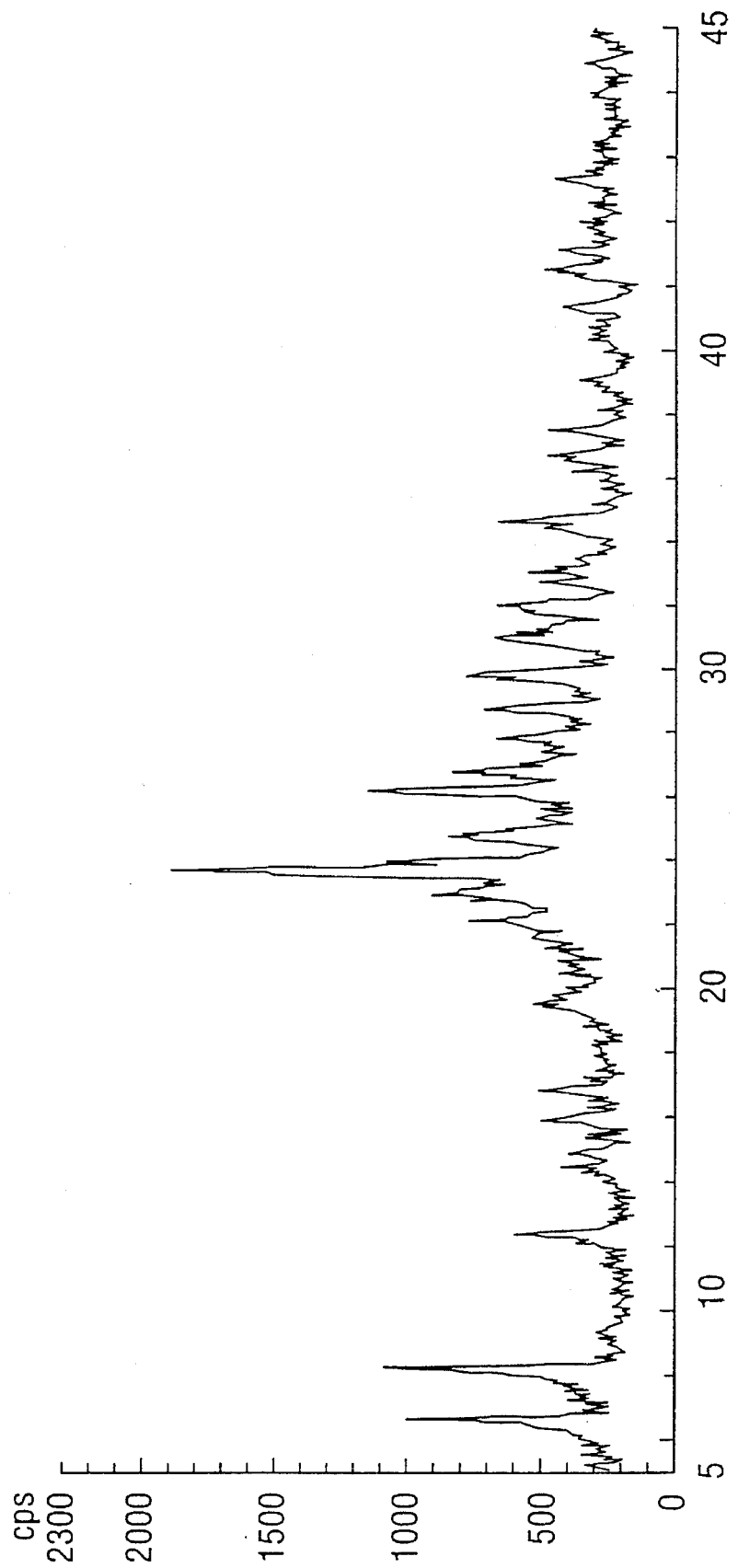
FIG. 2 is a powder X-ray diffraction pattern of the crystalline potassium (+)-(5R, 6S)-6-[(R)-1-hydroxyethyl]3-(3-pyridyl)-7-oxo-4-thia-1-azabicyclo [3.2.0]hept-2-ene-2-carboxylate of the present invention.

The diffraction pattern by powder X-ray diffraction pattern is shown in FIG. 2. As seen from FIG. 2, the crystalline potassium salt has a diffraction pattern which shows main peaks at spacing of 13.6, 11.2, 4.10, 4.05 and 3.7 Å.

EXAMPLE 1

An amorphous powder of (+)-(5R, 6S)-6-[(R)-1-hydroxyethyl]-3-(3-pyridyl)-7-oxo-4-thia-1-azabicyclo-[3.2.0]hept-2-ene-carboxylic acid pivaloyloxymethyl ester (19.5 g) obtained in the above Reference Example 1 was dissolved in ethanol (98 ml). This solution was heated to 31° C., followed by the addition of water which had been heated to 32° C. To the mixture was added an activated charcoal (Shirasagi P, manufactured by Takeda Chemical Industries, Ltd., 0.98 g) and the mixture was stirred for 10 minutes. Then, the activated charcoal was removed and washed with a mixed solvent of ethanol (20 ml) and water (29 ml). The filtrate was stirred at 25° to 30° C. for one hour, cooled to 10° C. and further stirred for one hour. The crystals deposited were filtered off, washed in turn with a mixed solvent of ethanol (20 ml) and water (39 ml) and further water (120 ml), and then dried under reduced pressure at 35° C. for 5 minutes to obtain crystals (16.6 g) of the ester as white powder.

Melting point: 95°–96° C.

Water content (Karl Ficher's method): 0.02%

Ethanol content (measured by gas chromatography): 0.03%

Powder X-ray diffraction pattern: The diffraction pattern is shown in FIG. 1.

EXAMPLE 2

The amorphous powder (1.18 g) of the ester obtained in the above Reference Example 1 was dissolved in ethyl acetate (12 ml), to which was added n-hexane (24 ml) with stirring. The solution thus obtained was stirred at 25° C. for 20 minutes, cooled at 5° C. and then allowed to stand for one hour. The crystals deposited were filtered off, washed with ethyl alcohol (9 ml) and then dried under reduced pressure to obtain crystals (0.84 g) of the ester.

Melting point: 95.5°–96° C.

IR (KBr method): 1766, 1714, 1320, 1138, 1106, 982 $cm^{-1}$

NMR ($CDCl_3$): δ 1.16 (9H, s), 1.38 (3H, d, J=6 Hz), 3.84 (1H, dd, J=1.5×6 Hz), 4.28 (1H, quint., J=6 Hz), 5.66, 5.77 (2H, ABq, J=5.5 Hz), 5.77 (1H, d, J=1.5 Hz), 7.2–8.7 (4H, m) ppm.

Powder X-ray diffraction pattern: It showed the same characteristic peaks as those obtained in Example 1.

EXAMPLE 3

A diluted ethyl acetate solution containing the ester (1530 g) obtained in the above Reference Example 1 was concentrated under reduced pressure until it because a viscose oily state. To the oily product was added ethyl ether (4.5 liters) and the mixture was stirred at 25° C. for 30 minutes and allowed to stand at 5° C. for 16 hours. The crystals deposited were filtered off, washed with ethyl ether (4.5 liters) and then dried under reduced pressure at 35° C. for about 7 hours to obtain crystals (the first crop of the crystals, 1131 g) of the ester.

Melting point: 96°–96.5° C.

The filtrate was concentrated under reduced pressure and to the resulting oily product (about 600 g) was added ethyl ester (1.2 liters), followed by stirring at 25° C. for 1.5 hours and further stirring at 5° C. for 30 minutes. The crystals deposited were filtered off, washed with ethyl ether (1.2 liters) and then dried under reduced pressure at 35° C. for about 3 hours to obtain crystals (the second crop of the crystals, 335 g) of the ester.

Powder X-ray diffraction pattern: Both first and second crops showed the same characteristic peaks as those in Example 1.

EXAMPLE 4

According to the following formulation, 50,000 tablets were prepared.

| Components | in one tablet (mg) | in 50,000 tablets (kg) |
|---|---|---|
| The crystals of the penem compound | 139 | 6.95 |
| Lactose | 28 | 1.4 |
| Corn starch | 26.4 | 1.32 |
| Hydroxypropyl cellulose | 6 | 0.3 |
| Magnesium stearate | 0.6 | 0.03 |
| Total | 200 | 10 |

The crystals of the penem compound of the present invention (6.95 kg), lactose (1.4 kg) and a part of corn starch (1 kg) were mixed in a fluidized pelletizer (FD-S-2, manufactured by Pawleck) and then 6% aqueous solution of hydroxypropyl cellulose (5 kg, corresponding to 0.3 kg of hydroxypropyl cellulose) was sprayed to obtain pellets. To the pellets thus obtained were added corn starch (0.32 kg) and magnesium stearate (0.03 kg) and the mixture was thoroughly mixed. The mixture was compressed by a rotary tabletting machine (clean press manufactured by Kikusui K. K., Japan) to obtain about 50,000 tablets of 8 mm in diameter.

EXAMPLE 5

Potassium (+)-(5R, 6S)-6-[(R)-1-hydroxyethyl]-3-(3-pyridyl)-7-oxo-4-thia-1-azabicyclo-[3.2.0]hept-2-ene-carboxylate (7.11 g) obtained in Reference Example 2 was dissolved in N,N-dimethylacetamide (100 ml) and the solution was cooled to −15° C. To the solution was added cyclohexyl-1-iodoethyl-carbonate (8.99 g) and the mixture was stirred at −10° C. for 30 minutes. To the mixture were added 5% (w/v) aqueous sodium thiosulfate solution (120 ml) and ethyl acetate (50 ml) to separate into layers and the aqueous layer was extracted with ethyl acetate (50 ml). The organic layers were combined and washed twice with saturated saline (120 ml) and dried over anhydrous magnesium sulfate (20 g). After concentration under reduced pressure, the residue was chromatographed on a silica gel column and eluted with ethyl acetate. The eluate was concentrated under reduced pressure to obtain a powder of (+)-(5R, 6S)-6-[(R)-1-hydroxyethyl]-3-(3-pyridyl)-7-oxo-4-thia-1-azabicyclo-[3.2.0]hept-2-ene-carboxylic acid 1-(cyclohexyloxy-carbonyloxy)ethyl ester.

NMR ($CDCl_3$: δ1.0–2.2 (10H, m), 1.38 (3H, d, J=6 Hz), 2.16 (3H, s), 2.63 (1H, br s), 3.84 (1H, dd, J=1.5×6.8 Hz), 4.1–4.5 (1H, m), 4.4–4.9 (1H, m), 5.78 (1H, d, J=1.5 Hz), 6.72 (1H, q, J=5.5 Hz), 7.2–8.8 (4H, m) ppm IR (KBr method): 2980, 1810, 1775, 1300, 1280, 1100 $cm^{-1}$ Experiment The crystalline powder of the ester produced according to the process of the present invention and the amorphous powder produced in the Reference Example 1 were stored at a dark place in a sealed container at a temperature of 60° C., respectively, and the residual rate was measured. The results are shown in Table 1 below.

TABLE 1

| Sample | Conditions of storage | Residual rate |
|---|---|---|
| Amorphous powder | 60° C., 14 days | 37.7% |
| Crystalline powder | 60° C., 19 days | 98.7% |

TABLE 1-continued

| Sample | Conditions of storage | Residual rate |
| --- | --- | --- |
| of Example 1 Crystalline powder of Example 2 | 60° C., 14 days | 98.9% |

The Acetoxymethyl Ester

The present invention also provides a crystalline acetoxymethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid, having a diffraction pattern which shows main peaks at spacings of 10.0, 7.1, 5.4, 4.5, 4.24, and 4.16 Å according to powder X-ray diffraction. The crystals can be obtained by dissolving amorphous acetoxymethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid in a good solvent and then adding thereto a poor solvent which is miscible with the good solvent, and stirring the obtained mixture. The present invention also provides a process of producing the crystals.

The amorphous acetoxymethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid (this free acid will be referred to "Compound [III]" hereinafter) to be used can be obtained by subjecting the corresponding sodium salt or potassium salt to esterification with chloromethyl acetate, bromomethyl acetate or iodomethyl acetate, in accordance with the method disclosed in U.S. Pat. No. 4,826,832 or the Journal of Antibiotics XLIII, No. 3, 306–313 (1990). The present inventors succeeded in obtaining seed crystals of acetoxymethyl ester of the Compound [III] by purifying the amorphous acetoxymethyl ester of the Compound [III] obtained as above by means of high performance liquid chromatography, dissolving the thus purified product in ethyl ether, adding isopropyl ether to the resulting solution and then leaving the obtained mixture standing at room temperature (about 25° C.), as described in the following Example 6. In general, compounds of this kind are considered to be difficult to obtain in crystalline form (Journal of Pharmaceutical Sciences, Vol. 66, No. 9, pp. 1312–1316 (September, 1977) discussed above). For example, as shown in the following Reference Examples 5 and 6, the present inventors attempted crystallization of the 1-(ethoxycarbonyloxy)ethyl ester, (5-methyl-2-oxo-1,3-dioxolene-4-yl)methyl ester, 1-acetoxyethyl ester, 1-(isobutoxycarbonyloxy)ethyl ester, cyclohexyloxycarbonyloxymethyl ester, 1-(isopropylcarbonyloxy)ethyl ester and 1-(cyclohexyloxycarbonyloxy)ethyl ester of the Compound [III] under various conditions in which the condition of this invention is involved, but no successful result was obtained. They have found that the acetoxymethyl ester of the present invention can be specifically crystallized under specific conditions.

The present inventors have unexpectedly found that the stable crystalline penem compound of the present invention is produced by the first step of dissolving the amorphous penem compound into a good solvent and the second step of adding to the solution a poor solvent which is miscible with the good solvent.

The amorphous penem compound is usually dissolved in a good solvent at a temperature of −10° C. to 40° C.

The good solvent to be used in the present invention is, for example, usually a solvent which dissolves not less than 30 mg, preferably not less than 100 mg of the amorphous penem compound per 1 ml of the solvent at room temperature (about 25° C.).

Examples of said good solvent include lower alcohols such as methanol, ethanol, propanol, isopropanol and the like, esters such as ethyl acetate and the like, ethyl ether and so on. The concentration of the amorphous penem compound to the good solvent is not specifically limited, but the concentration is preferably made as high as possible from the viewpoint of raising the yield of the crystals. Usually, the amount of the good solvent used is 1 to 300 ml, preferably 1 to 100 ml relative to 1 g of the amorphous penem compound. Additionally, in the present invention, without isolating said amorphous penem compound from the reaction mixture after the esterification process of the Compound [III], the reaction mixture may be diluted with said good solvent, then if desired, the resultant mixture may be purified according to the conventional means and concentrated, preferably under reduced pressure.

The poor solvent is added to the solution of the penem compound in the good solvent at a temperature of −10° C. to 40° C. The poor solvent to be used in the present invention is, for example, usually a solvent which dissolves not more than 10mg, preferably not more than 6 mg, of the amorphous penem compound per 1 ml of the solvent at room temperature (about 25° C.) and at the same time is miscible with the good solvent.

Examples of said poor solvent include isopropyl ether, hexane, petroleum ether, water and the like. When an alcohol is employed as the good solvent, water or hexane may be used as the poor solvent. Usually, the amount of the poor solvent used is 1 to 300 ml, preferably 1 to 100 ml to 1 g of the amorphous penem compound.

A sufficient volume of a poor solvent to be added may be one being enough to cause crystallization of the penem compound, and the volume ratio of the good solvent to the poor solvent is about 0.1 to 10, preferably 0.4 to 10, more preferably 0.4 to 3.0.

When a mixture of a good solvent and a poor solvent which contains the penem compound is stirred or left standing usually for 5 minutes to 2 hours at room temperature (−10° C. to 35° C.), crystallization of the penem compound is usually started. In this case, crystallization may be accelerated by, for example, rubbing the wall of a vessel or the like in accordance with the conventional manner. The mixture is then kept at 30° C. or below, preferably −10° C. to 15° C., and stirred or left standing for a further period ranging from 30 minutes to 20 hours to thereby complete the crystallization. The crystals thus obtained are washed with, e.g., hexane-ethanol, dried and isolated by the conventional processes.

The crystalline penem compound thus obtained according to the present invention has a melting point ranging from about 107° to 108° C. and shows a diffraction pattern having main peaks at spacings of 10.0, 7.1, 5.4, 4.5, 4.24 and 4.16 Å according to powder X-ray diffraction.

The crystalline penem compound is useful against various infections caused by bacteria as a stable antibacterial substance which shows a broad antibacterial spectrum by oral administration. For example, the crystalline penem compound has a minimal concentration of about 8 μg/ml or less for inhibiting the growth of gram-positive and gram-negative bacteria such as *Staphylococcus aureus, Staphylococcus pyogenes, Streptococcus pneumoniae, Streptococcus faecalis* and bacteria of the genus Neisseria. And, the crystalline penem compound of the present invention has a minimal concentration of about 64 μg/ml or/less for inhibiting the growth of gram-negative rod bacteria such as the genus Enterobacter, *Haemophilus influenza*, the genus Pseudomonas and the like, and anaerobic bacteria such as the genus Bacteroides. Further, in the general infection of mice caused by *Streptococcus aureus*, the crystalline penem compound shows $ED_{50}$ of about 0.5 to 15 mg/kg by oral administration.

For oral administration, the crystalline penem compound is formulated into the form of e.g. tablets or capsules according to the conventional methods. These tablets and capsules may contain diluents such as lactose, glucose, sucrose, mannitol, sorbitol, cellulose and glycine; lubricants such as silica, talc, stearic acid or its salts and polyethylene glycol; binders such as aluminum magnesium silicate, starch, gelatine, gums, cellulose derivatives and polyvinyl pyrrolidone; disintegrators such as starch and alginic acid or its salts; and various additives such as colorants, perfumes and sweeteners and the like among others.

While the dosage may vary depending upon the subject patients (mammals including human, dog, mouse, etc.) and their symptoms, for example, it ranges usually from about 50 mg to 1 g per day by oral administration to an adult of 70 kg weight to obtain the desired effect.

EXAMPLES

The following Reference Examples, Examples, Formulation Example and Experimental Example illustrate the acetoxymethyl ester aspect of the present invention in more detail, but the present invention should not be limited to them.

The symbols used in the following examples have the following significances:

s: singlet, br: broad, d: doublet, dd: doublet of doublet, q: quartet, dq: doublet of quartet, m: multiplet, ABq: AB-type quartet, $CDCl_3$: heavy chloroform, DMSO-$d_6$: dimethylsulfoxide-$d_6$, $D_2O$: heavy water, %: weight %

In NMR (nucleic magnetic resonance spectrum), unless otherwise specified, values of chemical shifts are shown in terms of δ value (ppm) measured by using tetramethyl silane or sodium 4,4-dimethyl-4-silapentanesulfonic acid (only when heavy water is employed) as the internal standard at 60 MHz or 90 MHz.

Reference Example 3

In 1.2 liter of tetrahydrofuran was suspended 67.3 g of potassium hydroxide. To the suspension was added 173.1 g of 2-ethyl hexanoic acid. The mixture was stirred until the potassium hydroxide was dissolved to obtain a solution of potassium 2-ethyl hexanoate.

In the mixture of 2.5 liters of methylene chloride and 1.3 liter of tetrahydrofuran was dissolved 332.4 g of allyl (+)-(5R, 6S)-6-[(R)-1-hydroxyethyl]-3-(3-pyridyl)-7-oxo-4-thia-1-azabicyclo[3.2.0]hept-2-ene-2-carboxylate. To the solution were added 26.2 g of triphenyl phosphine and 11.6 g of tetrakis(triphenylphosphine)palladium. To the mixture was added the above solution of potassium 2-ethyl hexanoate, then the mixture was stirred for 15 minutes. To the resultant mixture was added dropwise 7.5 liters of ethyl ether to cause precipitation of crystals, which was aged for 30 minutes while stirring. The crystals were collected by filtration and washed with 2.0 liters of ethyl ether. The crystals were dried under reduced pressure to give crude crystals of potassium (+)-(5R, 6S)-6-[(R)-1hydroxyethyl]-3-(3-pyridyl)-7-oxo-4-thia-1-azabicyclo[3-2-0]hept-2-ene-2-carboxylate.

The crude crystals were dissolved in a mixture of 460 ml of methanol and 230 ml of water. To the solution was added dropwise 7.0 liters of acetonitrile to cause precipitation of crystals. The mixture was aged one hour while cooling at 10° C. or below, and the crystals were collected by filtration and washed with 3.5 liters of acetonitrile, which was followed by drying under reduced pressure to give 323.0 g of crystals of potassium (+)-(5R, 6S)-6-[(R)-1-hydroxyethyl]-3-(3-pyridyl)-7-oxo-4-thia-1-azabicyclo[3.2.0]hept-2-ene-2-carboxylate.

Reference Example 4

In 75 ml of N,N-dimethyl acetamide was dissolved 5.33 g of crystals of potassium (+)-(5R, 6S)-6-[(R)-1-hydroxyethyl]-3-(3-pyridyl)-7-oxo-4-thia-1-azabicyclo[3.2.0]hept-2-ene-2-carboxylate. The solution was cooled to 5° C. and there was added dropwise 3.14 g of bromomethyl acetate. The mixture was stirred for 1.5 hour at the same temperature and there were added 150 ml of ethyl acetate and 120 ml of a 5% (w/v) aqueous solution of sodium thiosulfate. The mixture was separated into the ethyl acetate layer and the aqueous layer. To the aqueous layer was added 75 ml of ethyl acetate, which was shaken for extraction. Ethyl acetate layers were combined and washed with 120 ml each portions of a saturated aqueous saline solution three times. The resultant was dried over 5 g of anhydrous magnesium sulfate, then the solvent was distilled off to leave an oily substance. The oily substance was subjected to a silica gel (150 g) column chromatography, eluting with 300 ml of a mixture of ethyl acetate and hexane (4:1) and 600 ml of ethyl acetate, successively. Fractions containing desired substance, which show a peak at UV 254 nm, were combined and dried over 5 g of anhydrous magnesium sulfate, followed by distilling off the solvent under reduced pressure to afford 4.21 g of acetoxymethyl ester of (+)-(5R, 6S)-6-[(R)-1-hydroxyethyl]-3-(3-pyridyl)-7-oxo-4-thia-1-azabicyclo [3.2.0]hept-2-ene-2-carboxylic acid. NMR($CDCl_3$) δ 1.38 (3H,d, J=6 Hz), 2.06 (3H, s), 3.86 (1H,dd, J=1×6 Hz), 4.29 (1H, dq, J=6×6 Hz), 5.6 and 5.76 (2H,ABq, J=6 Hz), 5.78 (1H,d, J=1 Hz), 7.2–8.8 (4H,m) ppm This substance was in the state of hygroscopic powder and, when examiner microscopically under polarized light, no birefringence nor extinction was observed even by rotating the stage using crossed nicol, thus it was confirmed to be amorphous. And, the substance was confirmed to be amorphous also by X-ray diffraction.

Reference Example 5

About 5 mg of amorphous powder of 1-(isopropoxycarbonyloxy)ethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid was dissolved in about 0.5 ml of ethyl ether. To the solution was added about 0.5 ml of isopropyl ether, and the mixture was left standing at 25° C. for 1 hour to give an oily substance, but no precipitation of crystals was observed.

The following esters of the Compound [III] were subjected to the same procedure as above to attain the same result.

(1) 1-(Ethoxycarbonyloxy)ethyl ester
(2) (5-Methyl-2-oxy-1,3-dioxolen-4-yl)methyl ester
(3) 1-Acetoxyethyl ester
(4) 1-(Isobutoxycarbonyloxy)ethyl ester
(5) Cyclohexyloxycarbonyloxymethyl ester

Reference Example 6

By the same procedure as described in Example 6, 1.0g of 1-(cyclohexyloxycarbonyloxy)ethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid was subjected to purification to obtain two types of powdery products, respectively containing only one of the two diastereoisomers of the ester (∝ type: 0.35 g, β type: 0.35 g). About 2 mg of each of the thus purified two types of powdery products and of a mixture of these powdery products at a ratio of 1:1 was dissolved in about 0.2 ml of ethyl ether. To each of the three solutions was added about 0.2 ml of isopropyl ether, and the respective solutions were left standing at 25° C. for 1 hour only to obtain oily substances and no precipitation of crystals was observed.

EXAMPLE 6

Amorphous powder (1.0 g) of acetoxymethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid obtained above in Reference Example 4 was subjected to high performance liquid chromatography (Kurita System 300-W, manufactured by KURITA WATER INDUSTRIES LTD. in Japan), eluting with a mixture of 0.5% (w/v) aqueous solution of ammonium dihydrogenphosphate and acetonitrile (3:1). Fractions containing the desired compound were combined, followed by extraction with 320 ml of methylene chloride. The aqueous layer was further subjected to extraction with 160 ml of methylene chloride. The organic layers were combined and washed with 320 ml of 1% (w/v) aqueous solution of sodium hydrogen carbonate and 320 ml of saturated aqueous saline solution, successively, then dried over 50 g of anhydrous magnesium sulfate. The solvent was distilled off under reduced pressure to leave 0.84 g of the purified product of said ester in the state of powder.

About 2 mg of thus purified powdery product was dissolved in about 0.2 ml of ethyl ether at 25° C. To the solution was added about 0.2 ml of isopropyl ether at 25° C. The mixture was left standing at 25° C. for 1 hour to yield precipitates which were identified to be crystals through a microscope. The crystals were collected and dried to obtain white crystalline powder of the ester, m.p.107°–108° C.

EXAMPLE 7

Figure 3:
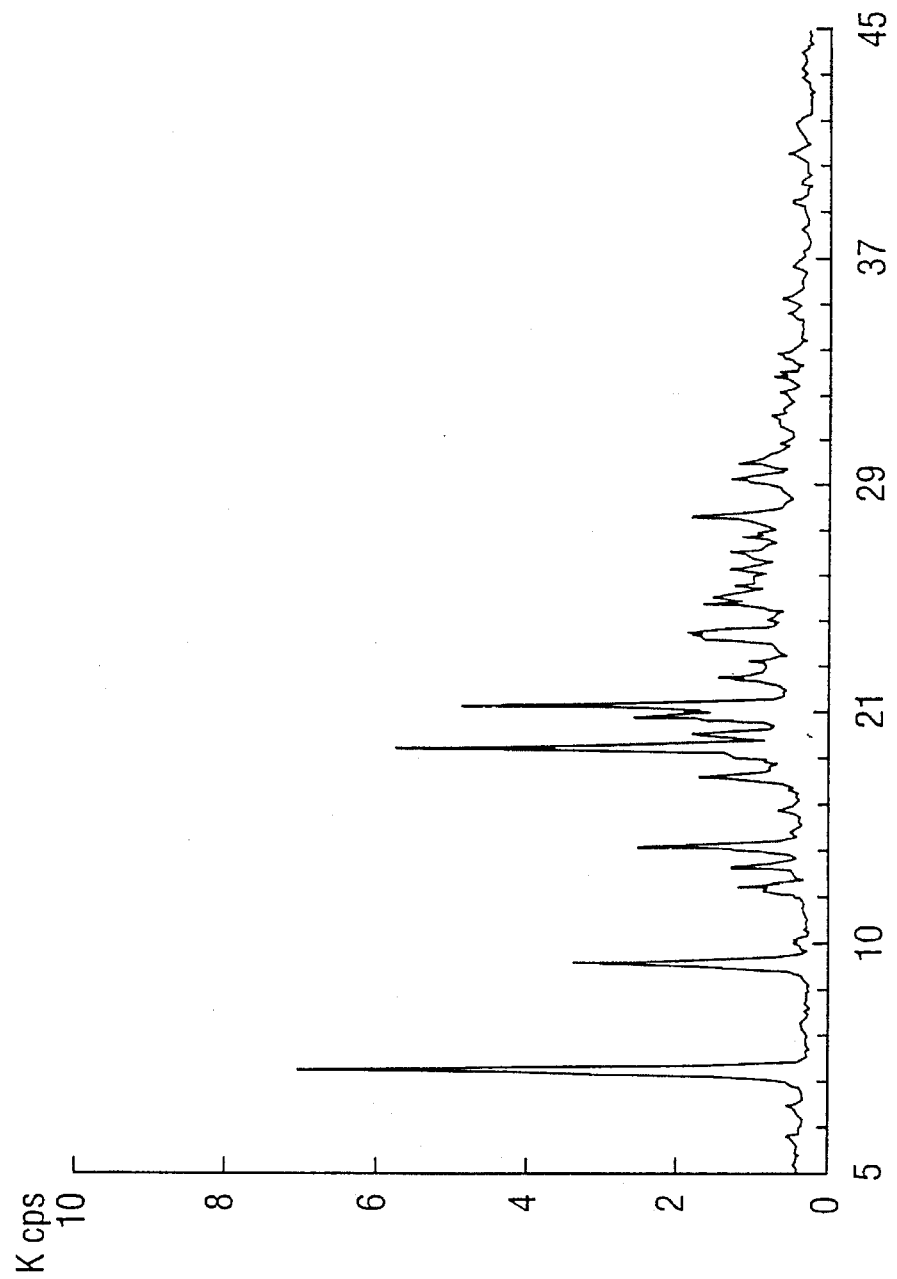
FIG. 3 is a powder X-ray diffraction pattern of the crystalline (+)-(5R, 6S)-6-[(R)-1-hydroxyethyl]-3-(3-pyridyl)-7-oxo-4-thia-1-azabicyclo [3.2.0]-hept-2-ene-2-carboxylic acid acetoxymethyl ester of the present invention.

In 5.0 ml of ethyl acetate was dissolved 1.00 g of amorphous powder of acetoxymethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid obtained in Reference Example 4, to which was added 2.5 ml of hexane at 25° C. To this solution was added about 0.1 mg of crystals of the ester, as seed crystals, obtained in Example 6. The mixture was stirred at 25° C. for 1 hour, whereupon crystals precipitated out. The mixture was cooled to 5° C. and aged while stirring for one hour. The crystals were collected by filtration, washed with 10 ml of a mixture of hexane and ethyl acetate (2:1) and dried under reduced pressure to afford 0.81 g of the white crystals of said ester, m.p. 107°–108° C. Powder X-ray diffraction pattern: Diffraction pattern is shown by FIG. 3 attached hereto.

EXAMPLE 8

In 3 ml of ethanol was dissolved 0.61 g of amorphous powder of the ester obtained in Reference Example 4, at 25° C. To this solution was added, as seed crystals, 0.1 mg of crystals of the ester obtained in Example 6. The mixture was stirred at 25° C. for 1 hour, whereupon crystals precipitated out. To the mixture was added 2.6 ml of hexane, which was cooled at 5° C. and aged for 4 hours, followed by filtration to collect the crystals. The crystals were washed with 15 ml of hexane and ethanol (2:1), and then dried under reduced pressure to afford 0.44 g of white crystals of the ester, m.p. 107°–108° C. Powder X-ray diffraction pattern: Showing characteristic peak similar to that of the product obtained in Example 7.

IR (KBr method): 1772, 1714, 1322, 1186, 982 cm$^{-1}$

NMR spectra: Agreement with those observed in Reference Example 4.

Formulation Example 1

| Components | in one tablet (mg) | in 50,000 tablets (kg) |
| --- | --- | --- |
| (1) The crystals of the penem compound (the compound obtained in Example 6 | 125 | 6.250 |
| (2) Lactose | 62.3 | 3.115 |
| (3) Croscarmellose sodium | 6.4 | 0.320 |
| (4) Hydroxypropyl cellulose | 5.7 | 0.285 |
| (5) Magnesium stearate | 0.6 | 0.030 |
| Total | 200 | 10.000 |

The present crystals of the penem compound (6,250 kg) and lactose (3.115 kg) were mixed in a fluid-bed granulator (FD-S-2, manufactured by Pawleck in Japan) and then a 6% aqueous solution of hydroxypropyl cellulose (4.750 kg, including 0.285 kg in terms of hydroxypropyl cellulose) was sprayed to obtain granules. To the granules thus obtained were added sodium croscalmellose (0.320 kg) and magnesium stearate (0.030 kg) and the mixture was thoroughly mixed. The mixture was compressed by a rotary tabletting machine (CLEAN PRESS manufactured by KIKUSUI SEISAKUSHO LTD. in Japan) to obtain about 50,000 tablets of 8 mm diameter.

Experimental Example

Samples of crystalline powder of the ester obtained in Example 8 and amorphous power of the ester obtained in Reference Example 4 were respectively stored in sealed vessels at 40° C., 50° C. and 60° C. for three days under protection from light. The said samples were also stored in sealed vessels at −20° C. as contrast. Respective residual rates of the esters are shown in Table 2.

Method to Measure the Residual Rate (%)

The respective residual rate (%) of the ester was measured by High Performance Liquid Chromatography under the following conditions.

Column: Inertsill ODS-2 (4.6 mm×150 mm)

Mobile Phase: 0.5% $NH_4H_2PO_4$:$CH_3CN$=75:25

Detect: UV 254 nm

TABLE 2

| Storing Conditions | Residual Rate | |
|---|---|---|
| | Amorphous Powder of Ref. Ex. 2 | Crystalline Powder of Ex. 3 |
| 40° C. | 95.6% | 101.9% |
| 50° C. | 83.7% | 101.7% |
| 60° C. | 55.8% | 102.2% |

As shown in Table 2, the crystals of the penem compound obtained by the present invention show excellent storability as compared with the amorphous powder thereof.

According to the present invention, acetoxymethyl ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid showing excellent antibacterial activity can be obtained as crystals showing favorable characteristic of storability. The crystals are remarkably advantageous when used for formulating them as medicinal preparations.

What is claimed is:

1. A crystalline ester of (+)-(5R, 6S)-6-[(R)-1-hydroxyethyl]-3-(3-pyridyl)-7-oxo-4-thia-1-azabicyclo[3.2.0]hept-2-ene-2-carboxylic acid which is the pivaloyloxymethyl or acetoxymethyl ester of said acid.

2. The crystalline ester of claim 1 which is the acetoxymethyl ester of said acid.

3. The crystalline ester of claim 2 including a diffraction pattern which shows main peaks at spacings of 10.0, 7.1, 5.4, 4.5, 4.24 and 4.16 A according to X-ray pattern diffraction.

4. The crystalline ester of claim 1 which is the pivaloyloxymethyl ester of said acid.

5. The crystalline ester of claim 4 including a diffraction pattern which shows main peaks at spacings of 12.8, 8.8, 5.6, 4.44, 4.36 and 4.2 A according to X-ray pattern diffraction.

6. An antibacterial agent which comprises a therapeutically effective amount of the crystalline penem compound of claim 1 and a pharmaceutically acceptable carrier or diluent.

7. A method for treating or preventing a bacterial infectious disease, which comprises administering to a mammal in need thereof a therapeutically effective amount of the crystalline penem compound of claim 1.

* * * * *